United States Patent [19]

Winchell et al.

[11] 4,233,285
[45] * Nov. 11, 1980

[54] MERCAPTOCARBOXYLIC ACID RADIOPHARMACEUTICALS

[75] Inventors: Harry S. Winchell, Lafayette; Tz-Hong Lin, Berkeley, both of Calif.

[73] Assignee: Medi-Physics, Inc., Emeryville, Calif.

[ * ] Notice: The portion of the term of this patent subsequent to Jun. 17, 1997, has been disclaimed.

[21] Appl. No.: 359,719

[22] Filed: May 14, 1973

[51] Int. Cl.$^2$ .................... A61K 29/00; A61K 43/00
[52] U.S. Cl. ................................. 424/1; 260/429.1; 424/9
[58] Field of Search ............... 424/1, 9; 250/303; 260/429.1; 252/429 R

[56] References Cited

U.S. PATENT DOCUMENTS

| | | | |
|---|---|---|---|
| 3,466,361 | 9/1969 | Richards et al. | 424/1 |
| 3,558,515 | 1/1971 | Kittleman et al. | 252/429 |
| 3,725,295 | 4/1973 | Eckelman et al. | 424/1 X |
| 3,749,913 | 7/1973 | Halpern et al. | 250/303 |
| 3,873,680 | 3/1975 | Jackson et al. | 424/1 |
| 3,928,552 | 12/1975 | Winchell et al. | 424/1 |

OTHER PUBLICATIONS

Tubis et al., "The Preparation of $^{99m}$Technetium-Labeled Cystine, Methionine, and Synthetic Polypeptide and their Distribution in Mice," in International Journal of Applied Radiation and Isotopes, vol. 19, No. 12, Dec. 1968, pp. 835–840.

Miller et al., "Spectrophotometric Determination of Technetium (VII) with Thioglycolic Acid," in Analytical Chemistry, vol. 32, #11, Oct. 1968, pp. 1429–1430.

Miller et al., "Spectrophotometric Determination of Technetium with Toluene-3;4-dithiol, in Analytical Chemistry, vol. 33, #3, Mar. 1961, pp. 404–406.

Al-Kayssi et al., "p-*Thiocresol as a Reagent for Technetium and Rhenium*," in Talanta, vol. 10, pp. 1047–1053, (1963).

Al-Kayssi et al., "*Spectrophotometric Studies on Technetium and Rhenium*," in Talanta, vol. 9, pp. 125–132 (1961).

Meyer et al., Separation and Spectophotometric Determination of Technetium in Fissium, vol. 36, #10, Sep. 1964, pp. 1975–1979.

Chemical Abstracts, vol. 78, #6, Feb. 12, 1973, Item No. 37529r.

*Primary Examiner*—Benjamin R. Padgett
*Assistant Examiner*—Christine M. Nucker
*Attorney, Agent, or Firm*—Jon S. Saxe; Bernard S. Leon; William H. Epstein

[57] ABSTRACT

Mercaptocarboxylic acid chelated heavy metal radioisotope pharmaceuticals and methods for making them.

9 Claims, No Drawings

MERCAPTOCARBOXYLIC ACID RADIOPHARMACEUTICALS

This invention relates generally to radiopharmaceuticals and more particularly to mercaptocarboxylic acid chelated heavy metal radioisotope pharmaceuticals useful for organ imaging.

Heretofore the metal chelating ability of some mercaptocarboxylic acids have been utilized for treatment of heavy metal poisoning and for other therapeutic purposes. For example, dimercaptosuccinic acid has been used to treat lead, mercury, arsenic and cadmium poisoning. Intravenous injections of a solution of the sodium salt of dimercaptosuccinic acid increase the urinary excretion of these metals from the human body. Salts of heavy metals, such as the sodium salt of antimony, chelated with dimercaptosuccinic acid are known to be effective in the clinical therapy of infestations by Schistosoma Mansoni and Schistosoma Haematobium.

The present invention employs a mercaptocarboxylic acid metal chelating agent containing at least one carboxyl group and at least one mercapto group, to chelate radioactive heavy metal ions for transport to various organs, tumors, etc. in the body for radioisotopic imaging purposes. The invention contemplates mono and dimercapto carboxylic and dicarboxylic acids.

One useful pharmaceutical is an improved renal imaging agent which consists of 2,3-dimercaptosuccinic acid chelating 99m-technetium in the presence of stannous ions as a reducing agent for the technetium. In vivo distribution studies of the labeled material in rats show that approximately 60% of the radioactivity remaining in the body one hour after intravenous injection is localized in the kidneys. This is a marked improvement in radioactivity retention in the renal parenchyma as compared to other 99m-technetium labeled pharmaceuticals utilized for renal imaging such as technetium labeled iron-ascorbate complex, polysaccharides or polypeptides. On the other hand, this imaging agent does not result in the high absorbed radiation dose and emissions of suboptimal gamma rays associated with radioisotopic organomercurial renal imaging agents.

Radioisotopic organomercurial agents also have been shown to be useful to image brain lesions (tumors and vascular lesions) and to localize directly in certain tumors and infarcted areas of the heart. But the high absorbed radiation dose associated with use of such agents and their suboptimal gamma ray emission have limited their application in study of the brain and in imaging tumors and myocardial infarcts. The close similarity in in vivo behavior of 99m-technetium labeled 2,3-dimercaptosuccinic acid to radioisotopic organomercurial agents, in view of the former's low absorbed radiation dose and optimal gamma emission, also indicate its utility in radioisotopic study of the brain, in imaging tumors and myocardial infarcts as well as in studying renal parenchymal morphology.

The principal object of this invention is to produce improved radiopharmaceuticals for delivery of radioactive heavy metal ions to body organs or to soft tissue tumors for diagnostic purposes.

An important object of the invention is to produce an improved renal parenchymal imaging radiopharmaceutical for delivering 99m-technetium to the kidney cortex.

Other objects of the invention are simple procedures for making the radiopharmaceuticals of this invention.

Other objects and advantages of the described radiopharmaceuticals and methods will become apparent upon consideration of the following description and specific examples.

The new pharmaceuticals of this invention consist of a mercaptocarboxylic acid, containing at least one carboxyl group and at least one mercapto group, chelating a heavy metal radionuclide. Among others mercaptoacetic acid, mercaptopropionic acid and mercapto and dimercaptosuccinic acid have been found to be useful. Labeling with a number of heavy metal ions is practical but 99m-technetium has been found to be particularly effective.

EXAMPLE 1

One improved radioisotopic renal parenchymal imaging agent of this invention is made from a prepared reagent that is an aqueous three millimolar solution of 2,3-dimercaptosuccinic acid and one millimolar stannous chloride at a pH of 2 to 4. The reagent is sterile and apyrogenic and can be prepared in advance of use and stored. To this reagent one adds just prior to use, oxidant-free sodium 99m-technetium pertechnetate in physiological saline solution in the proportion of 1 part by volume of reagent to 1 to 2 parts by volume of pertechnetate solution. The labeled material is thoroughly mixed, incubated at room temperature for 10 to 20 minutes and then can be used for intravenous injection.

Labeling can be performed in a shielded syringe by adding both reagent and pertechnetate solution to the same syringe and mixing thoroughly or by adding both solutions to a shielded mixing vial. The 99m-technetium labeled pharmaceutical should be used within thirty minutes after the incubation period.

The appropriate dose of the 99m-technetium labeled pharmaceutical for kidney imaging is between 1 and 5 mCi per adult patient. The specific concentration of 99m-technetium pertechnetate used in labeling the reagent should be such that less than 2 ml. of reagent is administered to a given patient. Administration should be intravenously to a well-hydrated patient. Scintigraphic imaging of kidneys can begin within one hour after administration. For best results one should wait two hours or more.

It has been discovered that the concentration of stannous chloride relative to 2,3 dimercaptosuccinic acid (DMSA) in the reagent is important. As shown on Table I solutions of 3 millimolar 2,3-dimercaptosuccinic acid (0.547 milligrams per ml.) with varied concentrations of stannous chloride (0.05, 0.1, 0.5, 1, 2 and 3 m$\overline{M}$) were prepared. White precipitates formed in the last two solutions. They were not labeled. The first four solutions were clear. They were labeled by addition of an equal volume of 99 m-technetium pertechnetate in normal saline solution and the labeled pharmaceutical administered intravenously to rats. In vivo distribution of radioactivity was determined one hour after injection for each concentration of stannous chloride. Higher body activity and lower kidney uptake were observed for the 0.05, 0.1 and 0.5 m$\overline{M}$ stannous chloride solutions as compared to the 1 m$\overline{M}$ solution shown on Table I.

Solutions of 1 m$\overline{M}$ stannous chloride also were prepared containing varied amounts of 2,3-dimercaptosuccinic acid (1,2,3,4, and 5 m$\overline{M}$) as shown in Table II. Higher concentrations of 2,3-dimercaptosuccinic acid were not studied because of its limited solubility in water. Precipitates formed in solutions containing 1, 2, 4 and 5 mM̄ organic acid immediately after addition of the stannous chloride. Millipore filtered (0.45 microns) solutions of 1, 2, 4 and 5 mM̄ and unfiltered 3 mM̄ solutions were mixed one to one by volume with 99m-technetium pertechnetate in normal saline solution. The in vivo distribution in rats was studied one hour after intravenous injection. No significant difference in in vivo distribution was noted between unfiltered 3 mM̄ and the filtered 4 mM̄ and 5 mM̄ 2,3-dimercaptosuccinic acid solutions. High liver uptake was observed for the filtered 1 and 2 mM̄ solutions. Accordingly, the critical proportion of 2,3-dimercaptosuccinic acid to stannous chloride was discovered to be the ratio of 3 mM̄ of the organic acid to 1 mM̄ of stannous chloride.

TABLE I

Effect of SnCl$_2$ Concentration on 3mM̄ DMSA Solution and Its In Vivo Distribution in Rats Activity in Various Tissues Expressed as % of Activity Remaining in Body at 1 Hour

| SnCl$_2$ (mM̄) | Precipitation | Kidneys | Liver and Spleen | Whole Blood (1 ml) | Rest of Body |
|---|---|---|---|---|---|
| 3 | Yes | — | — | — | — |
| 2 | Yes | — | — | — | — |
| 1 | No | 60.0 | 3.1 | 0.9 | 36.0 |
| 0.5 | No | 40.2 | 4.7 | 1.6 | 53.5 |
| 0.1 | No | 27.0 | 4.9 | 1.5 | 66.6 |
| 0.05 | No | 14.2 | 4.8 | 1.5 | 79.5 |

TABLE II

Effect of Concentration of 2,3-Dimercaptosuccinic Acid per One mM of Stannous Chloride Activity in Various Tissues Expressed as % of Activity Remaining in Body at 1 hour

| DMSA mM̄ | Precipitation | Kidneys | Liver and Spleen | Whole Blood (1 ml) | Rest of Body |
|---|---|---|---|---|---|
| 1 | Yes | 7.0 | 87.2 | 1.0 | 4.8 |
| 2 | Yes | 44.2 | 26.1 | 1.2 | 28.5 |
| 3 | No | 62.1 | 4.8 | 1.5 | 31.6 |
| 4 | Yes | 64.7 | 2.8 | 1.0 | 31.5 |
| 5 | Yes | 63.4 | 4.0 | 1.1 | 31.5 |

As is shown on Table III, pH also is important in making the foregoing pharmaceutical. Solutions of 3 mM̄ 2,3-dimercaptosuccinic acid and 1 mM̄ stannous chloride (pH 2.4-2.6) were prepared and the pH adjusted using hydrochloric acid or bicarbonate ion solutions in the pH range of 1-7.5 (1.0, 2.5, 4.0, 6.3 and 7.5). The dissolved 2,3-dimercaptosuccinic acid precipitated at pH 1.0. Colloidal stannous chloride precipitation was observed at pH 6.3 and 7.5. The solutions at pH 2.5 and 4 and Millipore filtered solutions at pH 6.3 and 7.5 were mixed 1 to 1 by volume with 99-m-technetium pertechnetate in normal saline solution and the in vivo distribution in rats studied one hour after intravenous administration of the labeled pharmaceutical. No significant difference in the in vivo distribution was observed for the solutions with pH of 2.5 and 4. High body background activity accompanied by a sharp decrease in kidney uptake were noted in the solutions of higher pH. The critical pH range for making the pharmaceutical is 2-4.

TABLE III

Activity in Various Tissues Expressed as % of Activity Remaining in Body at 1 Hour

| pH | Precipitation | Kidneys | Liver and Spleen | Whole Blood (1 ml) | Rest of Body |
|---|---|---|---|---|---|
| 1 | Yes | — | — | — | — |
| 2.5 | No | 65.0 | 3.6 | 1.0 | 30.4 |
| 4 | No | 63.3 | 4.7 | 0.6 | 31.4 |
| 6.3 | Yes | 13.0 | 2.1 | 0.4 | 84.5 |
| 7.5 | Yes | 9.9 | 2.6 | 0.6 | 86.9 |

Radiopharmaceuticals utilizing other mercaptocarboxylic acids and radionuclide labels are useful in renal parenchymal imaging and show similar in vivo distribution. The following examples are typical.

EXAMPLE II 5 milligrams of mercaptosuccinic acid per milliliter of 1 mM̄ stannous chloride in 0.01 N HCl were mixed with an equal volume of the 99m-pertechnetate solution of Example I and after incubation the mixture injected intravenously in rats. At one hour about 60% of the remaining activity localized in the kidney parenchyma.

EXAMPLE III

Mercaptoacetic acid in the form of 10 milligrams of its calcium salt per ml. of 1 mM̄ stannous chloride in 0.01 N HCl were mixed with an equal volume of the 99m—pertechnetate of Example I and after incubation injected in rats. In excess of 70% of the radioactivity remaining after one hour was in the kidney parenchyma.

EXAMPLE IV

One milligram per ml. of 2 - mercaptopropionic acid was added to 1 mM̄ stannous chloride in 0.01 N HCl. This reagent was mixed with an equal volume of the 99m—pertechnetate of Example I and after incubation injected in rats. One hour after intravenous injection about 40% of the remaining radioactivity localized in the kidney parenchyma.

EXAMPLE V 3-mercaptopropionic acid in the same portion and with the same procedure as Example IV produced substantially the same results after intravenous injection.

EXAMPLE VI

The 2,3-dimercaptosuccinic acid of Example I was used to chelate antimony—117 m by mixture with antimony chloride in the III and V valency states and the mixture administered intravenously to rats. Significant accumulations of radioactivity in both cases were noted in the kidneys on whole body scintographs.

EXAMPLE VII

The 2, 3 -dimercaptosuccinic acid of Example I also was used to chelate indium—III. Indium chloride was added to the DMSA solution and the mixture administered intravenously to rats. While body scintographs showed significant retention of radioactivity in the kidneys up to two hours after administration.

The foregoing examples are illustrative of the improved pharmaceuticals and the methods for making them. The scope of the invention is defined in the appended claims.

We claim:

1. A radiopharmaceutical comprising a complex of a mercaptocarboxylic acid chelating agent having at least one carboxylic acid group and at least one mercapto group with a radioactive heavy metal ion produced by reduction with stannous chloride in the presence of the chelating agent wherein said complex is formed at a pH of from about 2 to 4 and the mole ratio of said metal chelating agent to stannous chloride present to reduce such metal ion is about three to one.

2. The radiopharmaceutical of claim 1 wherein said chelating agent is selected from the group consisting of mercaptoacetic acid, 2-mercaptopropionic acid, 3-mercaptopropionic acid, mercaptosuccinic acid and 2,3-dimercaptosuccinic acid.

3. The radiopharmaceutical of claim 2 wherein said agent is 2,3-dimercaptosuccinic acid and said heavy metal ion is technetium 99m.

4. A reagent for producing a radiopharmaceutical comprising an aqueous solution containing mercaptocarboxylic acid chelating agent having at least one carboxylic acid group and at least mercapto group, 99-m-technetium pertechnetate and stannous chloride, where the mole ratio of said chelating agent to stannous chloride is about 3 to 1 and the pH of said solution being from about 2 to about 4.

5. The composition of claim 4 wherein said chelating agent is selected from the group consisting of mercaptoacetic acid, 2-mercaptopropionic acid, 3-mercaptopropionic acid, mercaptosuccinic acid and 2,3-dimercaptosuccinic acid.

6. The composition of claim 4 wherein said agent is 2,3-dimercaptosuccinic acid.

7. A method of imaging the renal cortex, brain abnormalities, tumors and myocardial infarcts of a patient comprising intravenously injecting said patient with a radiopharmaceutical comprising a complex of a mercaptocarboxylic acid metal chelating agent with a radioactive heavy metal ion produced by reduction with stannous chloride, wherein said complex is formed at a pH of from 2 to 4 and the mol ratio of said metal chelating agent to stannous chloride present to produce metal ion is about three to one, and scanning with a suitable apparatus.

8. The method of claim 7 wherein said chelating agent is selected from the group consisting of mercaptoacetic acid, 2-mercaptopropionic acid, 3-mercaptopropionic acid, mercaptosuccinic acid and 2,3-dimercaptosuccinic acid.

9. The method of claim 8 wherein said metal ion is technetium-99m and said chelating agent is 2,3-dimercaptosuccinic acid.

* * * * *